United States Patent
Marchand et al.

(10) Patent No.: US 12,187,987 B2
(45) Date of Patent: Jan. 7, 2025

(54) NON-FOAMING PERACETIC COMPOSITIONS, METHODS, AND KITS FOR REMOVING BIOFILMS FROM AN ENCLOSED SURFACE

(71) Applicant: SANI-MARC INC., Victoriaville (CA)

(72) Inventors: Patrick Marchand, G6P 8B5 (CA); Audrey-Anne Lafond, Notre-Dame du bon Conseil (CA)

(73) Assignee: SANI-MARC INC., Victoriaville (CA)

( * ) Notice: Subject to any disclaimer, the term of this patent is extended or adjusted under 35 U.S.C. 154(b) by 58 days.

(21) Appl. No.: 16/869,918

(22) Filed: May 8, 2020

(65) Prior Publication Data

US 2021/0087499 A1   Mar. 25, 2021

Related U.S. Application Data

(60) Provisional application No. 62/905,736, filed on Sep. 25, 2019.

(51) Int. Cl.
| | |
|---|---|
| C11D 3/39 | (2006.01) |
| C11D 1/02 | (2006.01) |
| C11D 1/04 | (2006.01) |
| C11D 1/72 | (2006.01) |
| C11D 1/722 | (2006.01) |
| C11D 3/04 | (2006.01) |

(52) U.S. Cl.
CPC .............. C11D 3/3945 (2013.01); C11D 1/02 (2013.01); C11D 1/04 (2013.01); C11D 1/72 (2013.01); C11D 1/722 (2013.01); C11D 3/042 (2013.01); C11D 2111/16 (2024.01); C11D 2111/18 (2024.01); C11D 2111/20 (2024.01)

(58) Field of Classification Search
CPC .. C11D 1/722; C11D 1/72; C11D 1/90; C11D 3/0026; C11D 3/042; C11D 3/2075; C11D 3/39; C11D 3/3902; C11D 3/3945; C11D 3/3955; C11D 7/08; C11D 9/42; C11D 9/446; C11D 2111/20; C11D 2111/14; C11D 2111/16

See application file for complete search history.

(56) References Cited

U.S. PATENT DOCUMENTS

| | | | |
|---|---|---|---|
| 4,587,264 A | 5/1986 | Jourdan-Laforte et al. | |
| 6,080,712 A * | 6/2000 | Revell .................. | C11D 3/3945 252/186.26 |
| 6,475,967 B1 * | 11/2002 | Arvanitidou ............ | C11D 1/94 510/435 |
| 9,034,390 B2 * | 5/2015 | Kielbania, Jr. ........ | A01N 59/00 514/553 |
| 2003/0045443 A1 * | 3/2003 | Korber ................. | C11D 3/2079 510/302 |
| 2005/0054875 A1 * | 3/2005 | Hei .................... | B01D 53/1418 562/2 |
| 2006/0233886 A1 * | 10/2006 | Kielbania, Jr. .......... | A61L 9/01 514/557 |
| 2009/0074881 A1 * | 3/2009 | Kielbania, Jr. ........ | A01N 37/36 424/618 |
| 2009/0221704 A1 | 9/2009 | Aksela et al. | |
| 2009/0324789 A1 * | 12/2009 | Ho ........................ | A01N 37/36 426/532 |
| 2010/0076082 A1 * | 3/2010 | Gamet ................. | C11D 3/2079 514/557 |
| 2010/0120656 A1 * | 5/2010 | McGee .................... | C11D 7/24 510/405 |
| 2011/0294408 A1 | 12/2011 | Hilgren et al. | |
| 2015/0232786 A1 * | 8/2015 | Dykstra ................. | C11D 3/391 252/186.42 |
| 2016/0135453 A1 * | 5/2016 | Pedersen ................ | A01N 37/00 514/557 |
| 2017/0128605 A1 * | 5/2017 | Franciskovich ..... | C11D 3/2068 |
| 2017/0158537 A1 | 6/2017 | Buschmann | |
| 2017/0208802 A1 * | 7/2017 | Franciskovich ....... | A01N 59/00 |

(Continued)

FOREIGN PATENT DOCUMENTS

| | | |
|---|---|---|
| CA | 2208785 C | 7/1996 |
| CA | 2785240 A1 | 6/2011 |
| CA | 3082443 A1 | 5/2019 |
| CA | 3103673 A1 | 6/2019 |
| CN | 104824042 A | 8/2015 |
| EP | 1829558 A1 | 9/2007 |
| JP | 2006052179 A | 2/2006 |
| JP | 2006206535 A | 8/2006 |

(Continued)

OTHER PUBLICATIONS

Hai Duong Ngoc Nguyen et al.: "Changes in resistance of Typhimurium biofilms formed under various consitions to industrial sanitizers," Food Control, Butterworth, London, GB, vol. 29, No. 1, Jun. 2, 2012, pp. 236-240.

(Continued)

*Primary Examiner* — Charles I Boyer
(74) *Attorney, Agent, or Firm* — Heslin Rothenberg Farley & Mesiti P.C.

(57) ABSTRACT

Described herein are peracetic compositions, methods and kits for the disruption and/or the removal of bacterial biofilms. The compositions comprise (i) peracetic acid; (ii) at least one secondary acid; and (iii) a non-foaming surfactant. One of the methods comprises contacting, preferably for at least 5 min, a surface with such a peracetic such a peracetic composition. Another method comprises circulating such a composition into a piping system for a period of time providing for disruption and/or removal from the biofilm. Kits may comprise bottles of concentrated solutions to be mixed and dilute with water before use. These compositions, methods and kits are particularly useful to remove bacterial biofilms from enclosed surfaces such as piping systems that are commonly used in the food and beverages industries.

14 Claims, 2 Drawing Sheets

(56) References Cited

U.S. PATENT DOCUMENTS

| | | | |
|---|---|---|---|
| 2017/0216471 A1* | 8/2017 | Franciskovich | A61L 2/186 |
| 2018/0187129 A1* | 7/2018 | Traistaru | C11D 3/3409 |
| 2019/0014777 A1* | 1/2019 | Myntti | A01N 59/00 |
| 2019/0092661 A1 | 3/2019 | Fast et al. | |
| 2019/0275468 A1* | 9/2019 | Schacht | B01D 71/022 |
| 2019/0284701 A1* | 9/2019 | Kim | C09K 13/06 |
| 2019/0380337 A1* | 12/2019 | Mittiga | A01N 37/16 |

FOREIGN PATENT DOCUMENTS

| | | |
|---|---|---|
| WO | 2008140974 | 11/2008 |
| WO | 2012044409 A1 | 4/2012 |
| WO | 2018112548 A1 | 6/2018 |

OTHER PUBLICATIONS

Ferey K et al., "Effects of Chemical Agents or Heat on Biofilm Removal From Tubing SUrfaces of Dialysis Machines," Journal of the American Society of Nephrology, vol. 12, 1001-09-01, p. 264X.

European Search Report, Application No. 20173619.6-1110, Dated Jul. 21, 2020.

Examination Report for Canadian Patent Application No. 3,080,524, Canada Intellectual Property Office, Jul. 8, 2021, 6 pages.

Cotillas S. et al., 2011, Electrochemical Synthesis of Peroxyacetic Acid Using Conductive Diamond Electrodes, Ind. Eng. Chem. Res., 50, 10889-10893.

Zhang T. et al., 2007, Peracetic Acid Synthesis by Acetaldehyde Liquid Phase Oxidation in Trickle Bed Reactor, Chinese Journal of Chemical Engineering vol. 15:320-325.

Bois R. et al., 2020, Screening of Surfactant Foaming Properties Using the Gas-Sparging Method: Design of an Optimal Protocol, J Surfactants Deterg., 23:359-369.

Kim and Huang, 2021, Reactivity of Peracetic Acid with Organic Compounds: A Critical Review, ACS ES&T Water 1:15-33.

Ecolab: Safety Data Sheet Vortexx, (Feb. 3, 2018), pp. 1-2.

ASTM D1173-07 (Reapproved 2015): Standard Test Method for Foaming Properties of Surface-Active Agents.

J. Ross, G. D. Miles: An Apparatus for Comparison of Foaming Properties of Soaps and Detergents, Oil & Soap, May 1941, p. 99-102.

"Bio-Soft N-Series Product Guide", Stepan,Company Sep. 2008.

BASF commercial brochure entitled "Product range—Home care and I&I solutions North America".

Ross-Miles Method.https://www.kruss-scientific.com/en/know-how/glossary/ross-miles-method.

* cited by examiner

NON-FOAMING PERACETIC COMPOSITIONS, METHODS, AND KITS FOR REMOVING BIOFILMS FROM AN ENCLOSED SURFACE

RELATED APPLICATION

The present application claims priority from U.S. provisional application No. 62/905,736 filed Sep. 25, 2019, the content of which is incorporated herein in its entirety.

FIELD OF THE INVENTION

The invention relates to the field of bacterial biofilms, and more particularly to compositions and methods for disruption and/or removal of bacterial biofilms.

BACKGROUND OF THE INVENTION

Bacterial biofilms are known to be a major source of food contamination thereby causing the recall and destruction of millions of dollars of food products each year. Biofilms are able to form on any type of surface, even under conditions normally preventing bacterial growth.

Biofilms can develop in piping systems, especially in the pipes, vessels, valves and fittings of piping systems that are commonly used in the milk, the brewery and the juice industry. Since it is nearly impossible or very difficult to have direct contact with the internal surface of the pipes, vessels, valves and fittings during the cleaning process, cleaning of these systems is generally carried out using a clean-in-place (CIP) method. The CIP method allows to clean the interior surfaces of pipes, vessels, process equipment, filters and associated fittings, without disassembly. Typically, a cleaning solution and/or disinfectant is pumped through the piping system for a given time (e.g. a minimum of 20 minutes) and the system is thereafter rinse with fresh water.

One of the limitations of CIP is that such cleaning system is relatively expensive and complicated to install because it requires at least three containers of solutions: a container for an alkaline cleaner, a container for an acid cleaner and a container of fresh water for rinsing. Therefore, in order to be accepted by customers and suit their needs, any new cleaning product must be conceived for being easily incorporated into existing CIP cleaning system, without requiring major modifications.

The use of peracid compositions to eliminate and/or control the growth of undesirable bacteria, including biofilms, has been described for instance in US patent applications US 2019/0092661 and US 2017/0158537, as well as in international PCT publication WO 2018/112548, WO 2012/044409 and WO 2008/140974. However, these compositions are not satisfactory because they have not proven to be sufficiently effective in removing biofilms and/or because they do not properly address the particular needs of CIP cleaning, especially for the highly regulated food and beverage industries.

Accordingly, there is a need for a composition that can effectively remove bacterial biofilms from piping systems, even with only a reduced contact time with the biofilm as it is typically required in CIP cleaning methods.

There is also a need for a composition effective against biofilms that is non-foaming in order to avoid undesirable fluctuations of pressure in piping systems that typically occurs when using foaming cleaning compositions.

There is also a need for a cleansing composition that can meet the high standards of the food and beverage industries.

The present invention addresses these needs and other needs as it will be apparent from reviews of the disclosure and description of the features of the invention hereinafter.

BRIEF SUMMARY OF THE INVENTION

According to one aspect, the invention relates to a composition for disruption and/or removal of a bacterial biofilm from a surface, comprising: (i) peracetic acid; (ii) at least one secondary acid; and (iii) a non-foaming surfactant.

According to another aspect, the invention relates to a composition for disruption and/or removal of bacterial biofilms from a surface, comprising (or consisting of):
 (i) about 0.03% w/w to about 15% w/w peracetic acid;
 (ii) about 0.01% w/w to about 30% w/w of at least one secondary acid selected from the group consisting of nitric acid, sulfuric acid, methane sulfonic acid, citric acid, phosphoric acid, hydrofluoric acid, hydrochloric acid, glycolic acid, formic acid, octanoic acid, phthalic acid, lactic acid, and combinations thereof;
 (iii) about 0.001% w/w to about 5% w/w of a non-foaming surfactant;
 (iv) less than about 0.1% w/w peroxide; and
 (v) about 5% w/w to about 99.8% w/w water.

According to another aspect, the invention relates to a method of disruption of biofilm on, and/or removal of biofilm from, a surface, comprising contacting said surface with a composition as defined herein.

According to another aspect, the invention relates to a method of disruption of biofilm on, and/or removal of biofilm from, an enclosed surface of a piping system, the method comprising circulating into said piping system a composition as defined herein, wherein said circulating is carried out for a period of time providing for disruption and/or removal from the biofilm.

According to another aspect, the invention relates to a clean-in-place (CIP) system for cleaning an interior surface of pipes and/or vessels, said CIP system comprising a supply container for receiving a cleaning composition, said supply container comprising a composition as defined herein.

According to another aspect, the invention relates to a kit for disruption of biofilm on, and/or removal of biofilm from, a surface, said kit comprising:
 a composition as defined herein; and
 at least one additional components selected from the group consisting of a user manual or instructions, a spray bottle, a mixing bottle, a mixing pump, pen(s), marking sheets, boxes, holders, wipes, and cleaning solutions.

In such kit, the composition may be in powder form, or the composition may formulated as a liquid concentrate for a dilution prior use.

According to another related aspect, the invention concerns a kit for disruption of biofilm on, and/or removal of biofilm from, a surface, the kit comprising:
 a first bottle comprising a first concentrated solution, the first concentrated solution comprising about 3% w/w to about 30% w/w peracetic acid, and about 0.2 001% w/w to about 5% w/w of a surfactant; and
 a second bottle comprising a second concentrated solution, the second concentrated solution comprising about 1% w/w to about 50% w/w of at least one secondary acid.

The kit may further comprise instructions for mixing the first and second concentrated solutions to obtain a ready-to-use solution, e.g. a diluted RTU solution. In one embodiment, the RTU comprises at least 400 ppm of PAA and at least 0.1% of the secondary acid. Water may be added during the mixing to obtain a diluted RTU solution having desired concentrations.

Additional aspects, advantages and features of the present invention will become more apparent upon reading of the following non-restrictive description of preferred embodiments which are exemplary and should not be interpreted as limiting the scope of the invention.

BRIEF DESCRIPTION OF THE DRAWINGS (OR FIGURES)

In order for the invention to be readily understood, embodiments of the invention are illustrated by way of example in the accompanying drawings.

FIG. 1 is a panel with pictures showing removal and detachment biofilms in different aqueous solutions. 1st column: water; 2nd column: PAA (400 ppm)+a surfactant (0.40.001% w/w Tergitol™); 3rd column: PAA (400 ppm)+ 0.04% w/w nitric acid. Briefly *P. aeruginosa* were first grown on glass disks. These disks were then deposited in each of the aqueous solutions for 20 min (1st row of pictures). After the 20-min period, the solutions were neutralized by adding a neutralisation solution, the disks were rinsed and observed with the naked eye (2nd row of pictures) or under a microscope (3rd row of pictures) for evaluating the remaining quantity of bacteria at the surface of the disks.

Figure 1:
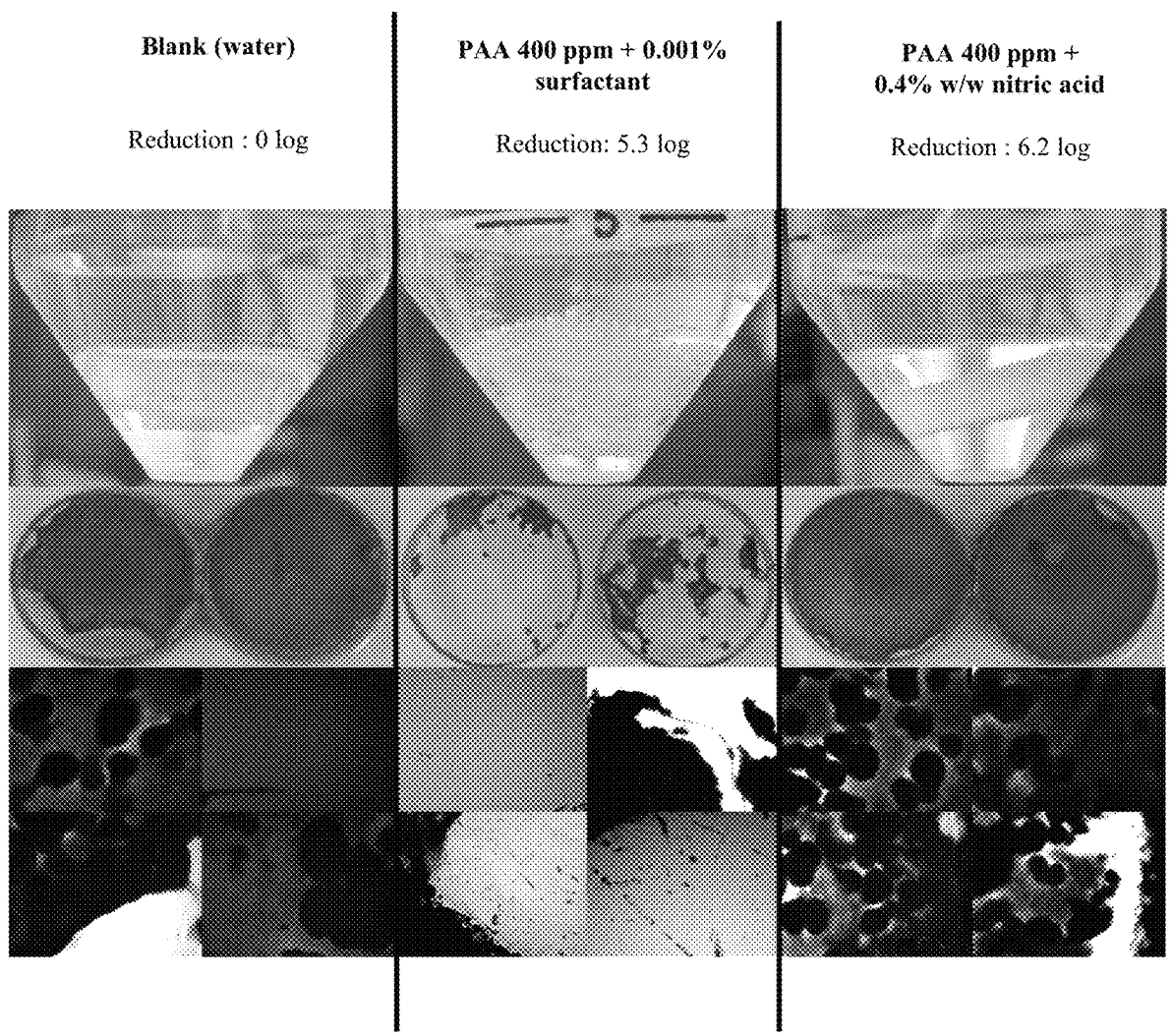

Further details of the invention and its advantages will be apparent from the detailed description included below.

DETAILED DESCRIPTION OF EMBODIMENTS

In the following description of the embodiments references to the accompanying drawings are illustrations of an example by which the invention may be practiced. It will be understood that other embodiments may be made without departing from the scope of the invention disclosed.

Biofilms Removal Compositions

According to one aspect, the invention relates to a composition comprising: (i) peracetic acid; (ii) at least one secondary acid; and (iii) a surfactant, preferably a non-foaming surfactant. The composition of the invention has been devised for disruption and/or removal of bacterial biofilms that may be present on surfaces.

As used herein the term "peracetic acid" refers to the organic compound also known as peroxyacetic acid, or PAA, having the formula $CH_3CO_3H$. The peracetic acid according to the invention may be produced by any suitable method, including but not limited to, by the autoxidation of acetaldehyde ($O_2 + CH_3CHO \rightarrow CH_3CO_3H$) or by treatment of acetic acid with hydrogen peroxide ($H_2O_2 + CH_3CO_2H \rightleftharpoons CH_3CO_3H + H_2O$).

In embodiments, the composition of the invention comprises about 0.03% w/w to about 20% w/w, or about 0.04% or about 0.05%, or about 0.08%, or about 0.1% w/w, or about 0.5% w/w, about 1% w/w, or about 2% w/w, or about 5% w/w, or about 10% w/w, or about 15% w/w peracetic acid. In one preferred embodiment, the composition comprises about 0.04% w/w peracetic acid.

In embodiments, the composition comprises less than about 0.1% w/w, or less than about 0.05% w/w, or less than about 0.01% w/w, or less than about 0.005%, or less than about 0.001% peroxide. In embodiments, the composition of the invention comprises no peroxide.

In embodiments, composition comprises a ratio of peracetic acid:peroxide that is at least 1.5:1, or at least 2:1, or at least 5:1, or at least 10:1, or at least 12.5:1, or at least 15:1, or at least 25:1, or at least 50:1, or at least 75:1, or at least 100:1.

As used herein the term "primary acid" refers to or implies presence of a first acid in a in peracetic acid (PAA) composition. As used herein PAA, is not considered as an "acid" but as an "oxidant". In accordance with the present invention, the term "primary acid" encompasses any acid that is used in the formation of peracetic acid.

In embodiments, the primary acid comprised in the composition of the present invention is selected from the group consisting of acetic acid, sulfuric acid and mixtures thereof. As is known, acetic acid may be reacted with hydrogen peroxide, in presence or absence of sulfuric acid (as a catalyzer) in the formation of peracetic acid.

As used herein the term "secondary acid" refers to an additional acid that is present in a peracetic acid (PAA) solution, in addition to a primary acid (if present). In accordance with the present invention, the term "secondary acid" encompasses any acid that is not used in the formation peracetic acid.

In embodiments the at least one secondary acid comprised in the composition of the present invention is selected from the group consisting of nitric acid, sulfuric acid, methane sulfonic acid, citric acid, phosphoric acid, hydrofluoric acid, hydrochloric acid, glycolic acid, formic acid, octanoic acid, phthalic acid, lactic acid, and combinations thereof. In embodiments the at least one secondary acid is other than acetic acid. In embodiments the at least one secondary acid is other than sulfuric acid.

In embodiments, the composition of the invention comprises about 0.01% w/w to about 30% w/w, or about 0.02% w/w, or about 0.04% w/w, or about 0.06% w/w, or about 0.1% w/w, or about 0.5% w/w, or about 1% w/w, or about 2% w/w, or about 5% w/w, or about 10% w/w, or about 20% w/w, or about 30% w/w of the at least one secondary acid. In one preferred embodiment, the composition comprises about 0.4% w/w of at least one secondary acid.

These adds may be used individually or as mixtures of two or more. In addition the lithium, sodium, potassium, and ammonium salts of these acids (monosalts or multiple cation salts) can be used in the present invention. The use of acid salts can increase the solubility of acids of low water solubility and can be used to change or raise the pH of formulations of the present invention. Those skilled in the art will appreciate that the examples of acids and acid salts listed above are not an exhaustive list of the acids that may be used in the present invention. One skilled in the art will recognize additional members and variations within the various categories listed above. Such additional compounds are considered to be within the scope of the present invention.

The composition of the invention further comprises a surfactant. Preferably the surfactant is a non-foaming surfactant in order to avoid undesirable fluctuations of pressure in piping systems that typically occurs when using foaming cleaning compositions.

In embodiments, the composition of the invention comprises about 0.001% w/w to about 10% w/w, or about 0.002% w/w, or about 0.003% w/w, or about 0.004% w/w, or about 0.005% w/w, or about 0.01% w/w, or about 0.02% w/w, or about 0.04% w/w, or about 0.06% w/w, or about 0.08% w/w, or about 0.1% w/w, or about 0.5% w/w, or about 1% w/w, or about 2% w/w, or about 5% w/w, of the non-foaming surfactant.

The surfactant used in the present formulations may be anionic or non-ionic. In embodiments, the surfactant is an anionic surfactant. In embodiments, the surfactant is a non-ionic surfactant.

Examples of anionic surfactants include, but are not limited to, those members of the following classes of chemical compounds: alkyl aromatic sulfonates, alkyl sulfosuccinates, dialkyl sulfosuccinates, alkylethoxylated sulfosuccinates, dialkylethoxylated sulfosuccinates. Specific examples include: sodium dodecylbenzene sulfonate, disodium 2-ethylhexyl sulfosuccinate, sodium lauryl sulfosuccinate, sodium laurylethoxy sulfosuccinate.

Examples of non-ionic surfactants include, but are not limited to those members of the following classes of chemical compounds: alkyl ethoxylates, alkylaryl ethoxylates, ethylene oxide/propylene oxide diblock and triblock surfactants both linear and branched.

In some embodiments the non-foaming surfactant is selected from the group consisting of Antarox™ L61 (block copolymer EO/PO), Antarox™ LA-EP-16 (branched alcohol EO/PO), Pluronic™ 462 D (block copolymer EO/PO), Hartopol™ 25R2 (block copolymer EO/PO), Mirataine™ ASC (alkylether hydoxypropyl sultaine), Akypo™ LF-2 (Capryleth-9 carboxylic acid), Akypo™ LF-4 (ether carboxylic derivative) and combinations thereof.

In particular embodiments the surfactant is selected from the group consisting of alcohol C8-C10, propoxylated poly(ethylene oxide), and mixtures thereof.

A single surfactant of the types listed above may be used in the compositions of the invention. Alternatively, compositions that include multiple surfactants are also considered as within the scope of this present invention. The examples of surfactants listed above are not an exhaustive list of the surfactants that may be used in the present invention. One skilled in the art will recognize additional members and variations within the various categories listed above. Such additional compounds are considered to be within the scope of the present invention.

In embodiments the composition comprises a ratio of peracetic acid:surfactant that is at least 12.5:1. In embodiments, the ratio of peracetic acid:surfactant is between about 2.5:1 and about 25:1.

The composition of the present invention may additionally contain one or more anti-microbial agents, including but not limited to non-cationic anti-microbial agents. The non-cationic anti-microbial agents may be phenolics, halogenated phenolics, halogenated diphenyl ethers, halogenated carbonilides, water soluble or water insoluble peroxy oxidizing agents, for example, peroxides, peresters, peracids, percarbonates, persulfates or mixtures thereof.

The composition of the present invention may optionally contain a low molecular weight alcohol. As used herein, "low molecular weight alcohol" means, an alkyl alcohol wherein the alkyl group contains from one to eight carbon atoms. Specific examples include butyl alcohol, propyl alcohol, ethyl alcohol, methyl alcohol and 2-Butoxyethanol (butyl cellosolve).

The composition of the present invention may also include other additives, such as fragrance, colors, inorganic salts, inorganic acids, sequestrants, organic solvents, fillers, rheology modifiers, and thickeners.

Table A1 hereinafter provides one particular example of a ready-to-use (RTU) composition, in accordance with an embodiment of the present invention.

TABLE A1 ready-to-use composition

| Component | Concentration (% w/w) | Role |
|---|---|---|
| Water | 99.4298 | solvent |
| Nitric acid | 0.4 | secondary acid |
| Peracetic acid | 0.04 | active |
| Hydrogen peroxide | 0.025 | active |
| Hydroxyethylidene diphosphonic acid | 0.002 | stabilizer |
| Acetic acid | 0.1 | primary acid |
| Polyalkylene glycol | 0.0016 | Surfactant |
| Alcohol C8-C10, ethoxylated propoxylated Poly(ethylene oxide) | 0.0016 | surfactant |

The compositions of the invention may be formulated as a ready to use solution (i.e. as defined hereinabove) or as a liquid concentrate (e.g. 2×, 3×, 4×, 5×, 10×, 50× etc.) for further dilution with water, water solutions, alcohols, or alcohol solutions, etc. It may also be formulated as a powder for later dissolution in a suitable aqueous solution (e.g. water). For a composition formulated as a liquid and/or solid, required ingredients may be mixed with a predetermined volume of filtered or distilled water. If necessary, the resulting mixed solution may be adjusted to the desired pH by addition of suitable acidifying agents.

In one embodiment, the composition of the invention is provided as a kit comprising two different bottles: a first bottle comprising a first concentrated solution having peracetic acid and the surfactant; and a second bottle comprising a second concentrated solution with the secondary acid. In one embodiment, a ready-to-use solution is obtained by mixing both bottles and diluting same with water.

In embodiments the first concentrated solution comprises about 3% w/w to about 30% w/w peracetic acid, and about 0.001% w/w to about 5% w/w of a surfactant. In embodiments the first concentrated solution comprises about 4% w/w to about 20% w/w, or about 5% w/w to about 15% w/w peracetic acid. In embodiments the first concentrated solution comprises about 0.01% w/w to about 4% w/w or about 0.1% w/w to about 3% w/w of a surfactant. In one particular embodiment the first concentrated solution comprises about 15% w/w peracetic acid and about 0.003% w/w surfactant.

In embodiments the second concentrated solution comprises about 1% w/w to about 50% w/w of at least one secondary acid. In one particular embodiment the second concentrated solution comprises about 35-40% w/w (e.g. about 38% w/w) of at least one secondary acid.

In embodiments, the concentrations of each concentrated solution are such that mixing of said solutions provides at least 400 ppm of PAA and at least 0.1% of the secondary acid.

Table A2 hereinafter provides one particular example of a liquid concentrate in accordance with an embodiment of the present invention. In this embodiment the concentrate is sold as a kit comprising two bottles: Bottle A (comprising most of the components, including PAA) and Bottle B (comprising the secondary acid). In use, to obtain a diluted solution ready-to-use, one can dilute in water 1/375 (0.27%) of the solution from Bottle A and 1/500 (0.2%) of the solution from Bottle B.

TABLE A2

Kit for a liquid concentrate

| | Component | Concentration (% w/w) | Role |
|---|---|---|---|
| Bottle A | Water | 36.175 | solvent |
| | Peracetic acid | 15 | Active, primary acid |
| | Hydrogen peroxide | 9.375 | active |
| | Hydroxyethylidene diphosphonic acid | 0.75 | stabilizer |
| | Acetic acid | 37.5 | primary acid |
| | Polyalkylene glycol | 0.6 | surfactant |
| | Alcohol C8-C10, ethoxylated propoxylated Poly (ethylene oxide) | 0.0016 | surfactant |
| Bottle B | Nitric acid | 38 | secondary acid |
| | Water | 62 | solvent |

The compositions of the present invention containing the various components indicated hereinabove may be also be in the form of a viscous liquid, a liquid soap, a pasty mixture (e.g., a heavy-duty soap used by mechanics), or a semi-solid or a solid (e.g., a bar of soap).

The form may be adapted according to the desired use and will generally depends on the solids content of the formulation, and the present invention contemplates all of such forms, to the extent the form does not affect the anti-biofilm properties of the composition.

In embodiments the compositions according to the present invention provides for disruption and/or removal of bacterial biofilms resulting from growth of various bacterial species including, but not limited to, *S. aureus, P. aeruginosa, E. coli, Listeria innocua, Brevundimonas vesicularis* and *Pseudomonas fluorescens*.

Methods and Uses

According to additional aspects, the invention relates to the uses of the compositions according to the present invention, particularly for the disruption and/or removal of bacterial biofilms.

In embodiments the compositions are used in method for the disruption and/or removal of bacterial biofilms resulting from various bacterial species including, but not limited to, *S. aureus, P. aeruginosa, E. coli, Listeria innocua, Brevundimonas vesicularis* and *Pseudomonas fluorescens*.

According to one particular aspect, the invention relates to a method of disruption of biofilm on, and/or removal of biofilm from, an enclosed surface of a piping system that may comprise pipes, vessels, process equipment, filters, membranes, heat exchangers, valves and/or associated fittings.

In embodiments, the method of the invention allow to remove biofilms from different types of surface including, but not limited to, glass (e.g. borosilicate), stainless steel, plastics and Teflon™. In embodiments the surface is in an interior surface of a pipe or of a vessel (e.g. smooth stainless steel surface).

In one embodiment, the method comprises circulating into the piping system a composition as defined herein for a period of time providing for successful disruption and/or removal from the biofilm. Particularly, the circulating may be carried out for at least 5 minutes, or least 10 minutes, or at least 15 minutes, or at least 20 minutes, or at least 30 minutes or more. It is within the skill of those in the art to determine an acceptable period of time providing for a desired efficacy. Typically a longer period of time may be preferred to achieve better biofilm removal.

In embodiments the composition is so efficacious that a volume of about 0.1 ml of the composition on 1 cm$^2$ effectively disrupts and/or removes the biofilm. In embodiments, a volume of about 0.1 ml of the composition is sufficient to effectively disrupts and/or removes a biofilm comprising 4 log of bacteria per cm$^2$.

According to another particular aspect, the invention relates to a clean-in-place (CIP) system for cleaning an enclosed surface of pipes and/or vessels. In one embodiment the CIP system comprises a supply container for receiving a cleaning composition and said supply container comprises a composition for the removal of biofilms as defined herein.

In embodiments, the methods of the present invention find uses in cleansing or disinfection of piping systems that are used in the production of food products, including but not limited to meat, milk, beer, juice purée, vegetable purée and jam.

Kits

A further aspect of the invention relates to kits. The kits of the invention may be useful for the practice of the methods of the invention, particularly for disruption of biofilm on a surface, for removal of biofilm from a surface, and/or for cleaning an enclosed surface of pipes and/or vessels.

A kit of the invention may comprise one or more of the following components: (i) a composition as defined herein; and (ii) at least one additional components, including but not limited to: a user manual or instructions, a spray bottle, a mixing bottle, a mixing pump, pen(s), marking sheets, boxes, holders, wipes, and cleaning solutions, etc. In the kit the composition of the invention may be provided in a powder form. The composition and/or additional solutions may also be formulated as a liquid concentrate for a dilution prior use.

As indicated hereinbefore, kits in accordance with the present invention may also comprise two different bottles, each bottle having a different concentrated solution to be mixed and diluted with water in order to provide a final ready-to-use solution. Such kits may further comprise, among other things instructions for mixing the concentrated solutions in order to obtain the ready-to-use solution, a mixing vessel, a protective mask, protective gloves, etc.

Those skilled in the art will recognize, or be able to ascertain, using no more than routine experimentation, numerous equivalents to the specific procedures, embodiments, claims, and examples described herein. Such equivalents are considered to be within the scope of this invention, and covered by the claims appended hereto. The invention is further illustrated by the following examples, which should not be construed as further or specifically limiting.

EXAMPLES

Example 1: Unexpected Synergistic Effects on Biofilm Removal by Combining Peracetic Acid with a Secondary Acid As is known, peracetic acid (PAA) is highly acidic (pH ~2). Therefore, addition a secondary acid to a peracetic acid solution was not expected to have a major impact, if any, on biofilms removal from a surface. Surprisingly, it was found that there is a significant synergistic effect of adding a secondary acid to a peracetic acid solution. As demonstrated in Tables 1 and 2 hereinafter, it is possible to greatly reduce a required concentration of peracetic acid for achieving biofilm removal by adding a secondary acid.

Briefly, as series of tests were carried out to test the efficacy of various peracetic acid solutions in the disruption/removal of a bacterial biofilm from a surface. These tests were done using *Pseudomonas aeruginosa* bacteria in accordance with the procedures ASTM 2871-12 (Standard Test Method for Determining Disinfectant Efficacy Against Biofilm Grown in the CDC Biofilm Reactor Using the Single Tube Method) and ASTM 2562-12 (Standard Test Method For Quantification And Of *Pseudomonas Aeruginosa* Biofilm Grown With High Shear And Continuous Flow Using CDC Biofilm Reactor).

As shown, in Tables 1A, 1B and 1C, at least 800 ppm (0.08% w/w) of peracetic acid (PAA) is required to obtain a 5 log reduction of the number of bacteria which, in accordance with the ASTM 2871-12 method, is the required minimum of reduction to prove efficacy. As can be appreciated, the amount of peroxide in the composition did not impact on the efficacy of PAA solutions, considering that a similar killing efficiency was obtained in presence of different concentrations of peroxide (Tables 1A and 1B) or even in total absence of peroxide (Table 1C).

TABLE 1A

Bacterial killing with different concentrations of peracetic acid (PAA) using dilutions of a 5% active PAA/peroxide solution

| Concentration of PAA | Concentration of peroxide | log of reduction* (after 20 min of contact) |
|---|---|---|
| 400 ppm (0.8% w/w) | 1200 ppm (0.8% w/w) | <3.30 |
| 600 ppm (1.2% w/w) | 1800 ppm (1.2% w/w) | 3.43 |
| 800 ppm (1.6% w/w) | 2400 ppm (1.6% w/w) | 5.12 |
| 1000 ppm (2.0% w/w) | 3000 ppm (2.0% w/w) | >5.8 (Total kill) |
| 1200 ppm (2.4% w/w) | 3600 ppm (2.4% w/w) | 6.78 (Total kill) |

TABLE 1B

Bacterial killing with different concentrations of peracetic acid (PAA) using dilutions of a 15% active PAA/peroxide solution

| Concentration of PAA | Concentration of peroxide | log of reduction* (after 20 min of contact) |
|---|---|---|
| 400 ppm (0.27% w/w) | 400 ppm (0.27% w/w) | <3.30 |
| 600 ppm (0.4% w/w) | 600 ppm (0.4% w/w) | 3.82 |
| 800 ppm (0.53% w/w) | 800 ppm (0.53% w/w) | 4.69 |
| 1000 ppm (0.667% w/w) | 1000 ppm (0.667% w/w) | 6.35 (Total kill) |
| 1200 ppm (0.8% w/w) | 1200 ppm (0.8% w/w) | 6.78 (Total kill) |

TABLE 1C

Bacterial killing with different concentrations of peracetic acid (PAA) only (solution without no peroxide)

| Concentration of PAA | Concentration of peroxide | log of reduction* (after 20 min of contact) |
|---|---|---|
| 400 ppm (0.8% w/w) | 0 ppm | <3.10 |
| 600 ppm (1.2% w/w) | 0 ppm | 3.65 |
| 800 ppm (1.6% w/w) | 0 ppm | 4.24 |
| 1000 ppm (2.0% w/w) | 0 ppm | 6.81 (Total kill) |
| 1200 ppm (2.4% w/w) | 0 ppm | 6.52 (Total kill) |

Surprisingly, it was found that it is possible to increase efficacy of the PAA by adding a secondary acid to the composition. Indeed, as shown in Table 2, by adding a secondary acid such as of 0.06% w/w nitric acid, it is possible to achieve a similar 5 log reduction with twice less PAA, i.e. with only 400 ppm peracetic acid in the solution, instead of 800 ppm (c.f. Table 1A).

TABLE 2

Bacterial killing using a solution comprising a combination of i) peracetic acid (400 ppm) + peroxide (1200 ppm) and ii) different concentrations of a secondary acid

| Concentration of the secondary acid (nitric acid) | log of reduction of bacteria after 20 min of contacting* |
|---|---|
| 0.06% w/w | 4.11 |
| 0.12% w/w | 4.77 |
| 0.18% w/w | 6.5 (Total kill) |

Although the addition of the secondary acid enhanced the antibacterial efficacy, it did not improve efficacy of PAA in peeling off the biofilm from the surface. As shown in FIG. 1, PAA+nitric acid reduced bacterial count by 6.2 log compared to water (0 log) while having a minimal or no impact in removing of the bacterial biofilm from the surface (see $1^{st}$ and $3^{rd}$ columns of pictures). On the other hand, combining PAA+a surfactant reduced both the bacterial count and the attachment of the biofilm (see $2^{nd}$ column of pictures).

Example 2: Added Benefits of a Surfactant on Biofilm Removal

In view of the results of Example 1, it was decided to try improving the efficacy of the peracetic/secondary acid aqueous solution by adding a non-foaming surfactant, particularly with the objective to further increase peeling off of the biofilm.

Figure 2:
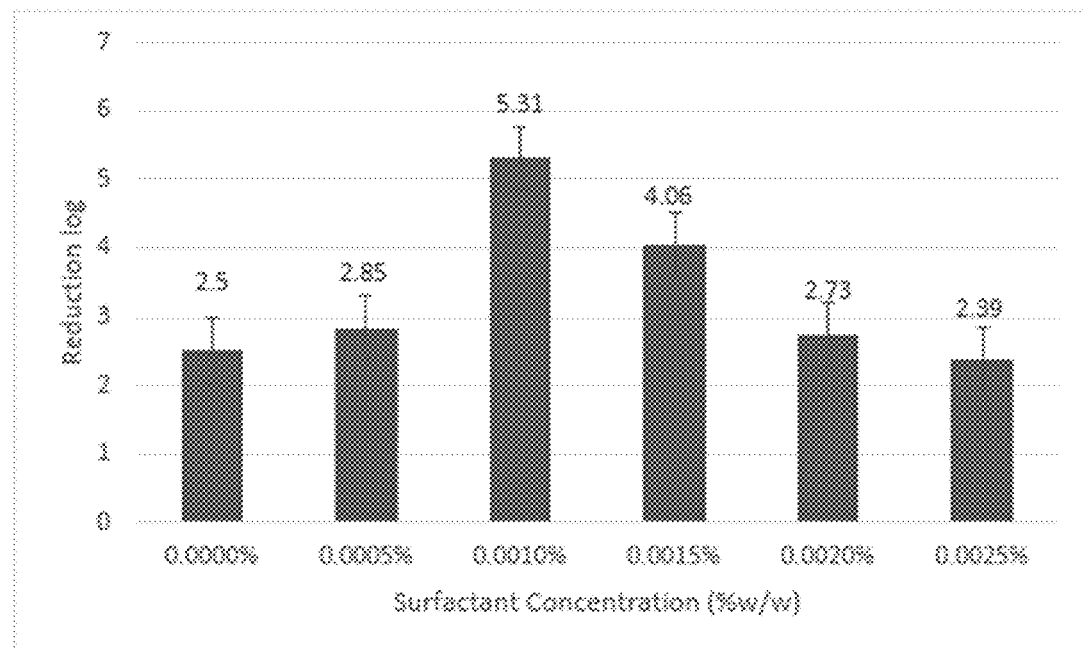
FIG. 2 is a bar graph showing the benefits of various concentrations of a surfactant (i.e. Tergitol™) when combined with 400 ppm of PAA, in reducing of the number of bacteria on a glass surface.

As shown in FIG. 2, addition of a surfactant, such as the non-foaming surfactant Tergitol™, had a synergistic effect with the action of 400 ppm PAA in reducing the number of bacteria on the glass surface. As illustrated in this figure, under the parameters of these tests, an optimal level of reduction was achieved using 0.001% w/w surfactant. These results suggest that the presence of the surfactant not only increases peeling of the biofilm from the surface (c.f. FIG. 1), it also increases the overall killing activity of PAA.

The efficacy of the composition of the invention in removing biofilms from different surfaces was also tested. As shown in Table 3, an aqueous solution comprising all the components, i.e. 400 ppm PAA, 0.4% w/w surfactant (Tergitol™) and 0.4% w/w nitric acid was highly effective in reducing of the number of bacteria on multiple surfaces, not only on glass, but also on stainless steel and Teflon™.

TABLE 3

Reduction of bacteria on multiple surfaces

| | Surface of bacterial growth | | |
|---|---|---|---|
| Bacterial conc. | Stainless steel | Borosilicate (glass) | Teflon ™ |
| Initial | 9.71 | 9.50 | 9.62 |
| After 20 min. | Total kill | Total kill | Total kill |

Although not shown, additional non-foaming surfactants were also tested and these additional surfactants were shown to have similar beneficial effects in the reduction of the number of bacteria. Table 4 below provides a list of non-foaming surfactants (anionic and non-ionic) that were shown to be successful in biofilm removal when combined with 400 ppm PAA.

TABLE 4

Non-foaming surfactants confirmed to assist PAA in the reduction of bacteria

| Commercial name | Chemical class or name | Surfactant type |
|---|---|---|
| Tergitol ™ L-62 ™ | Secondary polyether polyol (polyalkylene glycol) | non-ionic |
| Antarox ™ L61 | EO/PO block copolymer (polyalkylene glycol) | non-ionic |
| Antarox ™ LA-EP-16 | Branched EO/PO Alcohol (Oxirane, 2-methyl-, polymer with oxirane, monodecyl ether) | non-ionic |
| Triton ™ DF-12 | Polyethoxylated alcohol (Octenyl succinic acid) | anionic |
| Triton ™ DF-16 | Mixture of surfactants (Ethoxylated alcohols + polyethylene glycol) | non-ionic |
| Plurafac ™ SL F180 | Alcohol alkoxylate (fatty alcohol ethoxylated) | non-ionic |
| Pluronic ™ 462 D | EO/PO block copolymer | non-ionic |
| Hartopol ™ 25R2 | Polyoxypropylene-polyoxyethylene block copolymer (Polyoxyalkylene glycol ether) | non-ionic |
| Mirataine ™ ASC | Alkylether hydoxypropyl sultaine (Butylether Hydroxypropyl Sultaine + 2-Ethylhexylether Hydroxypropyl Sultaine) | anionic |
| Akypo ™ LF-2 | Capryleth-9 Carboxylic Acid | anionic |
| Akypo ™ LF-4 | Capryleth-9 Carboxylic Acid | anionic |

Overall, the present results show that it is possible to kill all the living bacteria (i.e. "total kill") and to remove at least 90% of an existing biofilm (c.f. FIG. 1) by contacting the biofilm for 20 min with an aqueous solution comprising 400 ppm PAA, 0.4% w/w of nitric acid, 0.001% w/w of a surfactant (anionic or non-ionic).

The present results also confirm that ratios of concentrations of PAA/secondary acid and ratios of concentrations of PAA/surfactants play a role in the disruption and/or removal of the biofilms, whereas the ratios of concentrations of secondary acid/surfactants do not.

The present examples also demonstrate that compositions comprising peracetic acid, at least one secondary acid and a non-foaming surfactant are highly effective in disrupting and/or removing bacterial biofilms from different surfaces and that peroxide is facultative and can thus be omitted.

Example 3: Added Benefits of a Surfactant on Bactericidal Efficacy

The composition in accordance with the invention was also tested for its bactericidal activity. Briefly, bactericidal activity of solutions comprising increasing concentrations of PAA, 0.1% w/w nitric acid ($HNO_3$) and a surfactant (polyalkylene glycol 0.002% w/w) were compared to corresponding solutions not comprising surfactant. The tests were carried out in vitro against *E. coli* at 20° C., 200 ppm of hardness and 0.03 g/l of soil load.

Figure 3:
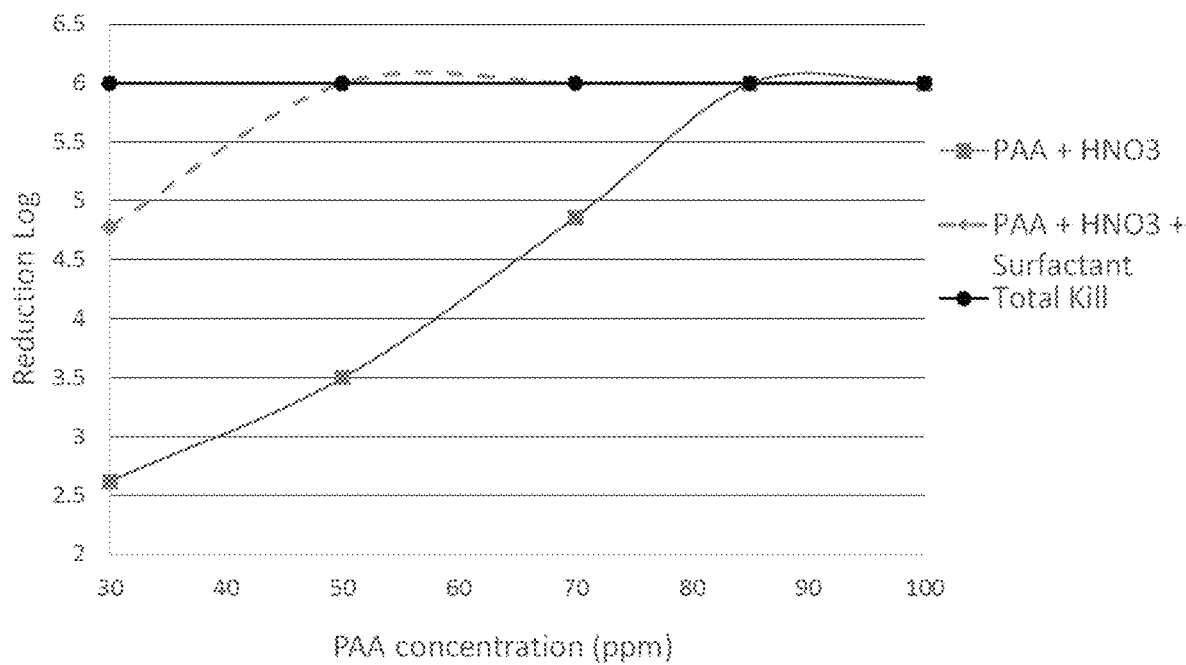
FIG. 3 is a line graph showing superior bactericidal efficacy of a combination PAA, nitric acid and a surfactant.

As shown in FIG. 3, the PAA solutions, with or without surfactant, were both effective in reducing bacterial count up to a total kill. However the solution further comprising the surfactant was much more effective in killing bacteria, with a total kill obtained with only 50 ppm PAA, whereas, in absence of the surfactant, as much as 85 ppm PAA was required for a total bacterial kill.

Altogether these examples support the efficacy against bacteria, and particularly against bacterial biofilms, of a composition comprising peracetic acid, at least one secondary acid, and a non-foaming surfactant.

Headings are included herein for reference and to aid in locating certain sections. These headings are not intended to limit the scope of the concepts described therein, and these concepts may have applicability in other sections throughout the entire specification. Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise. Thus, for example, reference to "a compound" includes one or more of such compounds and reference to "the method" includes reference to equivalent steps and methods known to those of ordinary skill in the art that could be modified or substituted for the methods described herein.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contains certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. An aqueous composition for disruption and/or removal of bacterial biofilms from a surface, comprising:
   (i) about 0.03% w/w to about 15% w/w peracetic acid;
   (ii) about 0.01% w/w to about 30% w/w of at least one secondary acid selected from the group consisting of nitric acid, sulfuric acid, methane sulfonic acid, citric acid, phosphoric acid, hydrofluoric acid, hydrochloric acid, glycolic acid, formic acid, octanoic acid, phthalic acid, lactic acid, and combinations thereof;
   (iii) about 0.001% w/w to about 5% w/w of a non-foaming surfactant;
   (iv) less than about 0.1% w/w peroxide; and
   (v) about 5% w/w to about 99.8% w/w water;
   wherein the non-foaming surfactant is selected from the group consisting of the product secondary polyether polyol (polyalkylene glycol) sold under the trademark Tergitol™ L-62™, the product EO/PO block copolymer (polyalkylene glycol) sold under the trademark Antarox™ L61, the product branched EO/PO alcohol (oxirane, 2-methyl-, polymer with oxirane, monodecyl ether) sold under the trademark Antarox™ LA-EP-16, the product polyethoxylated alcohol (Octenyl succinic acid) sold under the trademark Triton™ DF-12, the mixture of surfactants (ethoxylated alcohols+polyethylene glycol) sold under the trademark Triton™ DF-16, the product alcohol alkoxylate (fatty alcohol ethoxylated) sold under the trademark Plurafac™ SL F180, the product EO/PO block copolymer sold under the trademark Pluronic™ 462 D, the product polyoxypropylene-polyoxyethylene block copolymer (polyoxyalkylene glycol ether) sold under the trademark Hartopol™ 25R2, the product alkylether hydoxypropyl sultaine (butylether hydroxypropyl sultaine+2-ethylhexylether hydroxypropyl sultaine) sold under the trademark Mirataine™ ASC, the product capryleth-9 carboxylic acid sold under the trademark Akypo™ LF-2, the product capryleth-9 carboxylic acid sold under the trademark Akypo™ LF-4, and mixtures thereof.

2. A method of disruption of biofilm on, and/or removal of biofilm from, a surface, comprising contacting said surface with a composition according to claim 1.

3. The method of claim 2, wherein said contacting is for at least 5 minutes.

4. The method of claim 2, wherein a volume of about 0.1 ml of said composition contacted with a surface of 1 $cm^2$ effectively disrupts and/or removes said biofilm from said surface.

5. The method of claim 2, wherein a volume of about 0.1 ml of said composition is sufficient to effectively disrupts and/or removes a biofilm comprising 4 log of bacteria per $cm^2$.

6. The method of claim 2, wherein said method provides for disruption and/or removal of bacterial biofilms made of one or more of *S. aureus, P. aeruginosa, E. coli, Listeria innocua, Brevundimonas vesicularis* and *Pseudomonas fluorescens* bacteria.

7. The method of claim 2, wherein said surface is at least one of glass, stainless steel, plastic and Teflon™.

8. The method of claim 2, wherein said surface is inside a piping system comprising at least one of pipes, vessels, process equipment, filters, membranes, heat exchangers, and/or associated fittings.

9. A method of disruption of biofilm on, and/or removal of biofilm from, an enclosed surface of a piping system, the method comprising circulating into said piping system a composition according to claim 1, wherein said circulating is carried out for a period of time providing for disruption and/or removal from the biofilm.

10. The method of claim 9, wherein said circulating comprises circulating said composition into pipes, vessels, valves and/or fittings of said piping systems.

11. The method of claim 9, wherein said circulating is carried out for at least 5 minutes.

12. The method of claim 9, further comprising rinsing said piping system with water after said circulating.

13. The method of claim 9, wherein said method provides for disruption and/or removal of bacterial biofilms made of one or more of *S. aureus, P. aeruginosa, E. coli, Listeria innocua, Brevundimonas vesicularis* and *Pseudomonas fluorescens* bacteria.

14. The composition of claim 1, wherein the composition comprises a w/w ratio of peracetic acid:surfactant that is between about 2.5:1 and about 25:1.

* * * * *